United States Patent [19]

Petrofsky

[11] Patent Number: 4,580,569
[45] Date of Patent: Apr. 8, 1986

[54] APPARATUS AND METHOD FOR MUSCLE STIMULATION

[75] Inventor: Jerrold S. Petrofsky, Beavercreek, Ohio

[73] Assignee: Wright State University, Dayton, Ohio

[21] Appl. No.: 561,770

[22] Filed: Dec. 15, 1983

[51] Int. Cl.$^4$ ............................................. A61N 1/36
[52] U.S. Cl. ................................................ 128/420 A
[58] Field of Search ................................... 128/420 A

[56] References Cited

U.S. PATENT DOCUMENTS

| | | | |
|---|---|---|---|
| 3,774,620 | 11/1973 | Hansjurgens | 128/420 A |
| 3,895,639 | 7/1975 | Rodler | |
| 3,958,577 | 5/1976 | Rodler | 128/420 A |
| 4,023,574 | 5/1977 | Nemec | |
| 4,148,321 | 4/1979 | Wyss et al. | |
| 4,153,061 | 5/1979 | Nemec | 128/420 A |
| 4,280,504 | 7/1981 | Rodler | 128/420 A |
| 4,390,023 | 6/1983 | Rise | |
| 4,392,496 | 7/1983 | Stanton | |
| 4,401,121 | 8/1983 | Rodler | 128/420 A |
| 4,421,336 | 12/1983 | Petrofsky et al. | |

FOREIGN PATENT DOCUMENTS

| | | | |
|---|---|---|---|
| 525214 | 5/1956 | Canada | 128/420 A |
| 2143562 | 8/1972 | Fed. Rep. of Germany | 128/420 A |
| 2222844 | 11/1973 | Fed. Rep. of Germany | 128/420 A |
| 2745349 | 4/1978 | Fed. Rep. of Germany | 128/420 A |
| 2843922 | 4/1979 | Fed. Rep. of Germany | 128/420 A |
| 2937984 | 4/1981 | Fed. Rep. of Germany | 128/420 A |

OTHER PUBLICATIONS

Clinical Electric Stimulation-G. Keith Stillwell-pp. 125-129 (name of publication and publication date unknown).
Restoration of Hand Function in the Quadriplegic through Electrical Stimulation-Peckham & Mortimer-published 1977 by Marcel Dekker, Inc. in testbook entitled "Functional Electrical Stimulation".

Primary Examiner—William E. Kamm
Assistant Examiner—Mitchell J. Shein
Attorney, Agent, or Firm—Biebel, French & Nauman

[57] ABSTRACT

A system for stimulating a grasping action by a paralyzed hand. The system includes a sensor arrangement for detecting movement of a shoulder by the paralyzed person. The sensor transmits shoulder movement signals to a computerized controller which generates stimulation signals for stimulation electrodes mounted within a cuff worn about the forearm which supports the hand to be stimulated. Closed loop control is accomplished by use of a glove to which are attached a length sensor and a pressure sensor connected for alternative selection. Stimulation of deeply buried muscles is accomplished by arranging the stimulation electrodes into side-by-side electrode sets which are so positioned as to produce focusing of stimulation energy at the location of the subject muscle.

13 Claims, 15 Drawing Figures

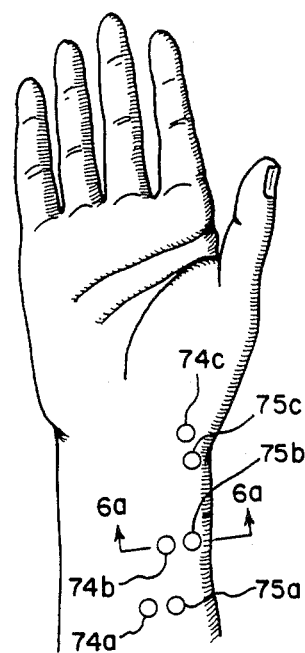
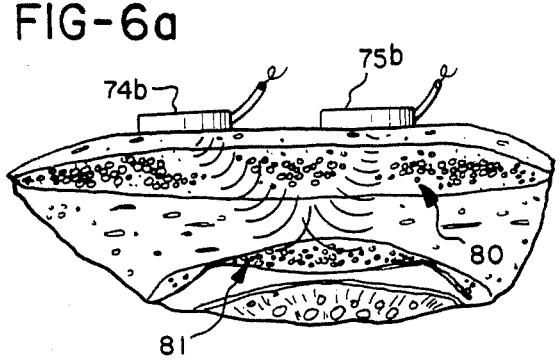
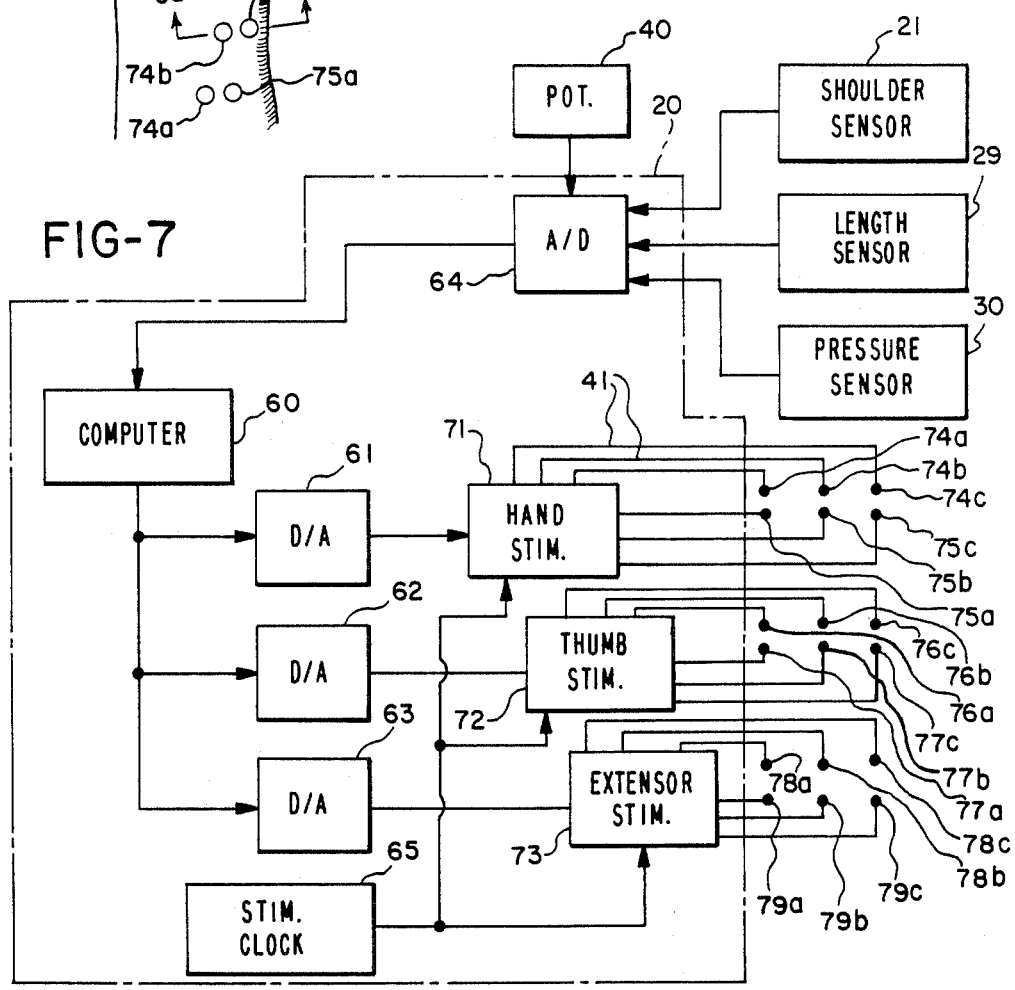

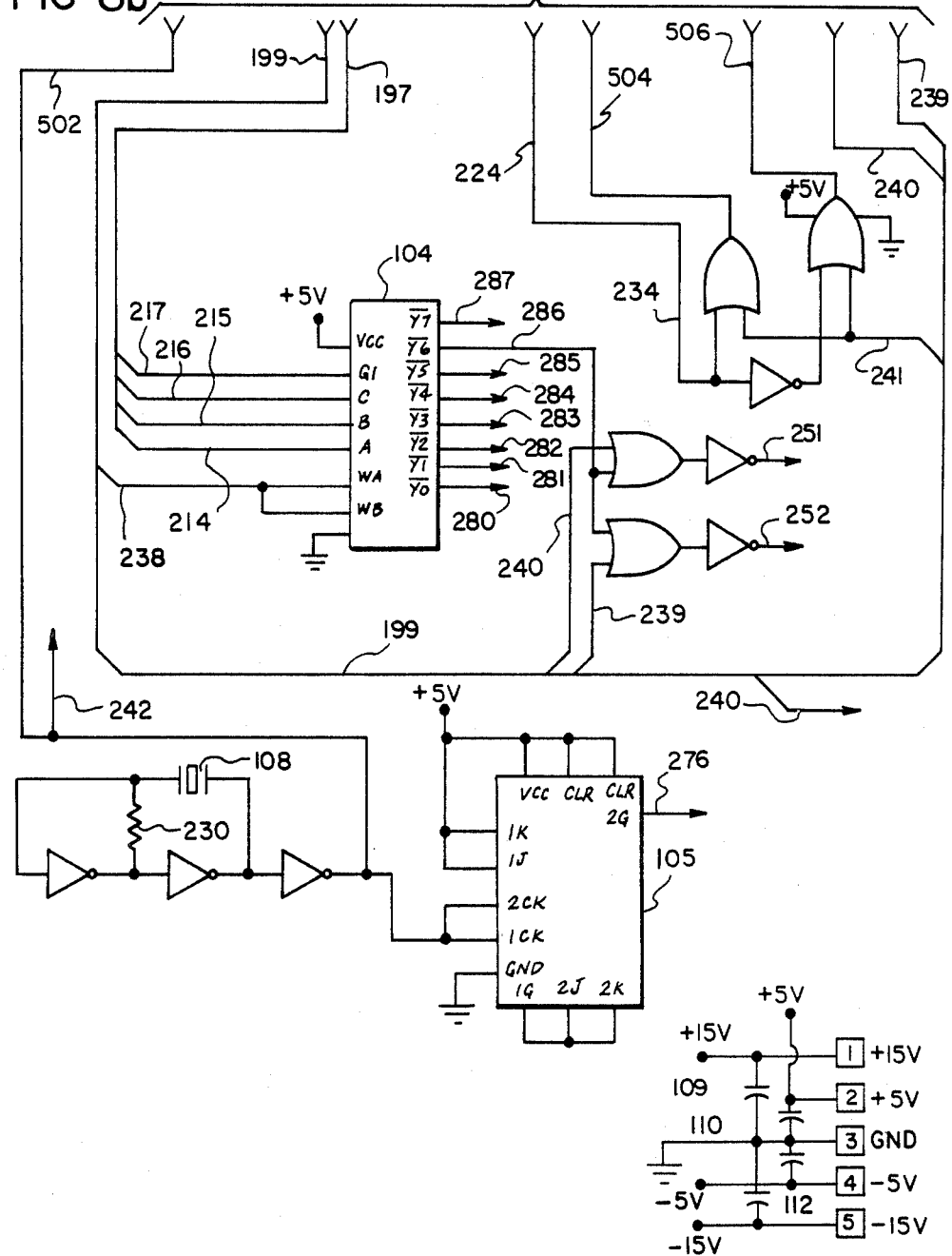

APPARATUS AND METHOD FOR MUSCLE STIMULATION

BACKGROUND OF THE INVENTION

This invention relates to muscle stimulation systems for paralyzed persons. More particularaly, the invention relates to apparatus and method for stimulating controlled contraction of a muscle buried deeply below the skin of a paralyzed person without stimulating contraction of an overlying superficial muscle.

Typical prior art devices for stimulating paralyzed muscles are described in Petrofsky et al U.S. application Ser. No. 444,647, filed Nov. 26, 1982 and in other references cited therein. These prior art systems have a set of three electrodes for each muscle group to be stimulated. The electrodes are placed on the surface of the skin above the muscle group to be stimulated and are excited by pairs of pulsed stimulating signals. One of the three electrodes is connected to a high voltage ground, and voltage pulses are applied between that electrode and the other two electrodes in alternating fashion. The series of pulses applied between the ground electrode and either of the other electrodes occur at a frequency of about 60 Hz, and these pulses are alternated with 60 Hz pulses applied between the ground electrode and the other active electrode. The pulse width is disclosed as being about 500 microseconds, and the pusle amplitude varies in accordance with the desired stimulation level up to a maximum of about 255 volts. Such stimulation produces recruitment of all motor units and results in maximum effort by the muscle. Feedback signals are provided in order to control the amplitude of the applied stimulation signals in an automatic manner.

The above-described stimulation technique has been utilized only for stimulation of leg muscles. Leg muscles have been so stimulated for operation of exercise equipment, for pedaling vehicles and for walking. The muscles which have been stimulated have been the quadriceps, iliac, gastrocnemius and hamstring groups. These muscles are relatively large and are easily accessible for surface stimulation.

It has been found that when prior art stimulation techniques are applied to the stimulation of a hand, serious problems arise. Hand flexing is controlled by the flexor digitorum profundus manus muscle group which is relatively small and which is deeply located below superficial muscles controlling other motions. The same is true of the adductor pollicis muscle group which controls thumb flexing and the extensor carpi ulnaris muscle group which controls wrist extension for hand opening. The prior art stimulation system has been found unsatisfactory for stimulating those muscles, because the desired muscle stimulation is accompanied by stimulation of the overlying superficial muscles. Accordingly, there has been a need to provide a stimulation system which is able to stimulate deeply buried muscles without stimulation of the overlying superficial muscles.

SUMMARY OF THE INVENTION

In accordance with this invention deeply buried muscles are stimulated by applying stimulation signals to surface electrodes arranged for focusing stimulation energy downwardly into the desired region. Apparatus in accordance with this invention includes first and second sets of electrodes which are placed in side by side relationship upon the skin above the muscle to be stimulated. Each set of stimulation electrodes is connected to a signal generator which generates a series of pulsed stimulation signals. The pulses comprising those stimulation signals have amplitudes which are insufficient for stimulating the superficial muscles, when applied to one set of electrodes. However, the pulse amplitude is sufficient for producing the desired result when applied to both sets of electrodes and focused downwardly toward the deeply buried muscle. It has been found, furthermore, that the pulses, so produced, are particularly effective if applied to the two sets of electrodes with a phase delay therebetween. A phase delay of approximately one millisecond is preferred.

It is therefore an object of this invention to provide apparatus and method for stimulating controlled contraction of a muscle buried deeply below the skin of a paralyzed person without stimulating contraction of overlying superficial muscles.

Other objects and advantages of the present invention will be apparent from the following description, the accompanying drawings, and the appended claims.

BRIEF DESCRIPTION OF THE DRAWINGS

FIG. 6 is an illustration of a human hand showing typical mounting locations for a set of stimulation electrodes which control flexing of the flexor digitorum profundus manus muscle group;

FIG. 6a is an enlarged cross section taken along lines 6a—6a of FIG. 6;

FIG. 7 is a schematic block diagram of a hand control system;

FIGS. 8a and 8b are a schematic diagram of a portion of a computer for a hand control system;

DESCRIPTION OF THE PREFERRED EMBODIMENT

Figure 1:
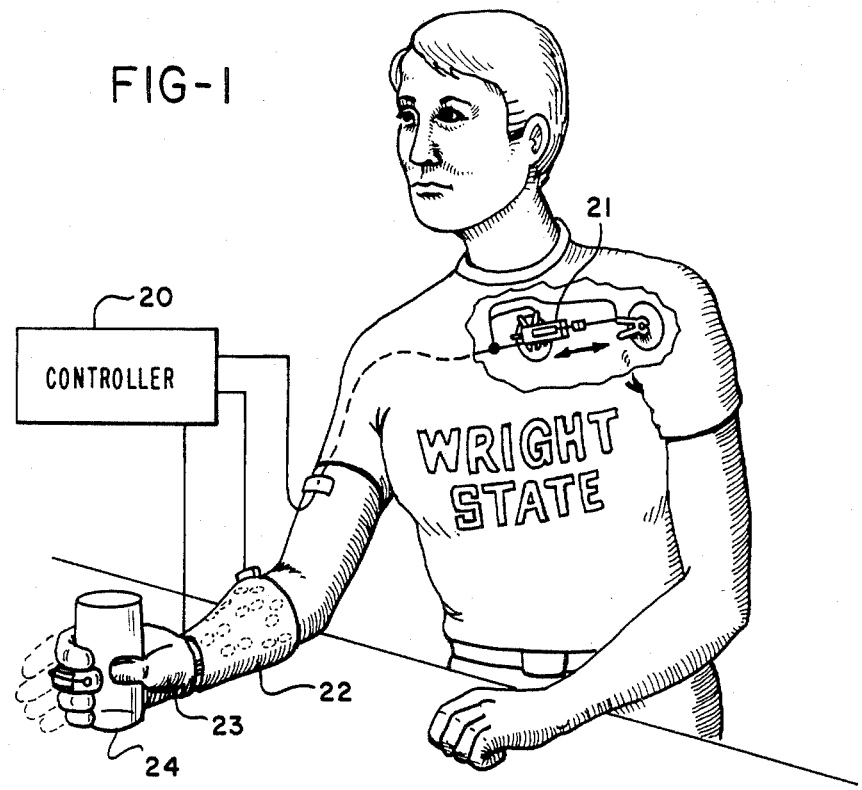
FIG. 1 is a schematic illustration of a hand control system mounted on the body of a quadriplegic person.

FIG. 1 illustrates a hand control system in accordance with the present invention as mounted on the body of a quadriplegic person. As illustrated therein, the system comprises shoulder sensor 21, a controller 20, a cuff 22 and a glove 23. Under control of the system the hand of the quadriplegic person may be stimulated to grasp an object such as a glass 24.

Figure 2:
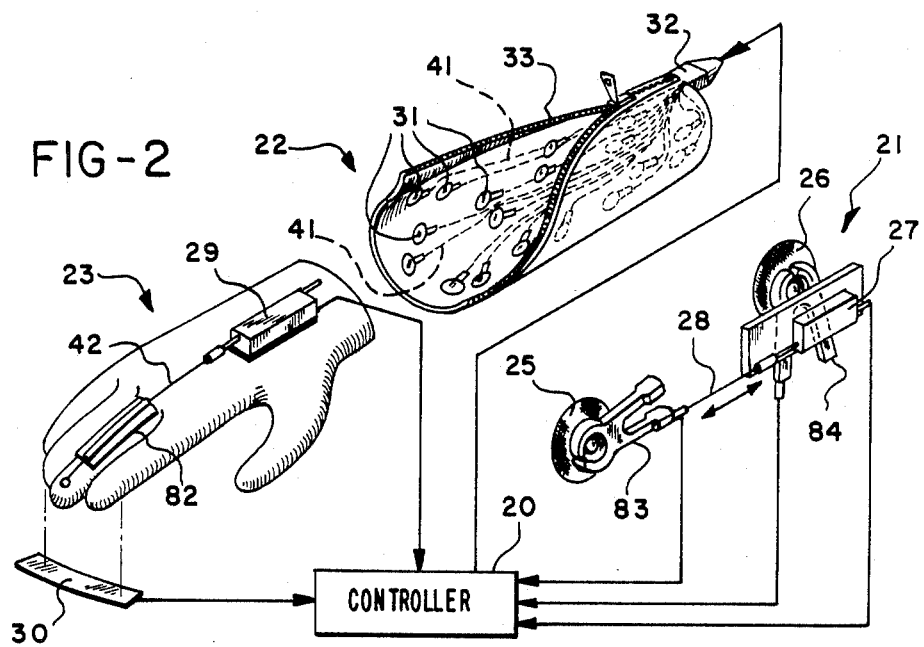
FIG. 2 is an enlarged view of the apparatus generally illustrated in FIG. 1.

As shown in more detail in FIG. 2, shoulder sensor 21 comprises a linear potentiometer connected to a sliding wire 28. Potentiometer 27 may be a device of the type sold by Bourns, Inc. under Part No. 2051414101. Potentiometer 27 is supported by a clip 84 attached to an ECG electrode 26. Electrode 26 may be a prejelled self-adhering disposable electrode of the type sold by NDM Corporation of Dayton, Ohio under Catalog No. 01-3330. Electrode 26 is adhered to the skin of the quadriplegic person opposite another similar electrode 25. There is a clip 83 attached to electrode 25 for supporting the end of the sliding wire 28. It will be seen that one of electrodes 25, 26 is attached to the shoulder of the quadriplegic person, while the other electrode is attached to the chest. Thus when the shoulder is flexed relative to the chest a sliding motion of wire 28 is produced. This causes movement of a pick-off across a resistor within potentiometer 27, thereby generating a variable voltage output for sensing by controller 20.

Figure 12:
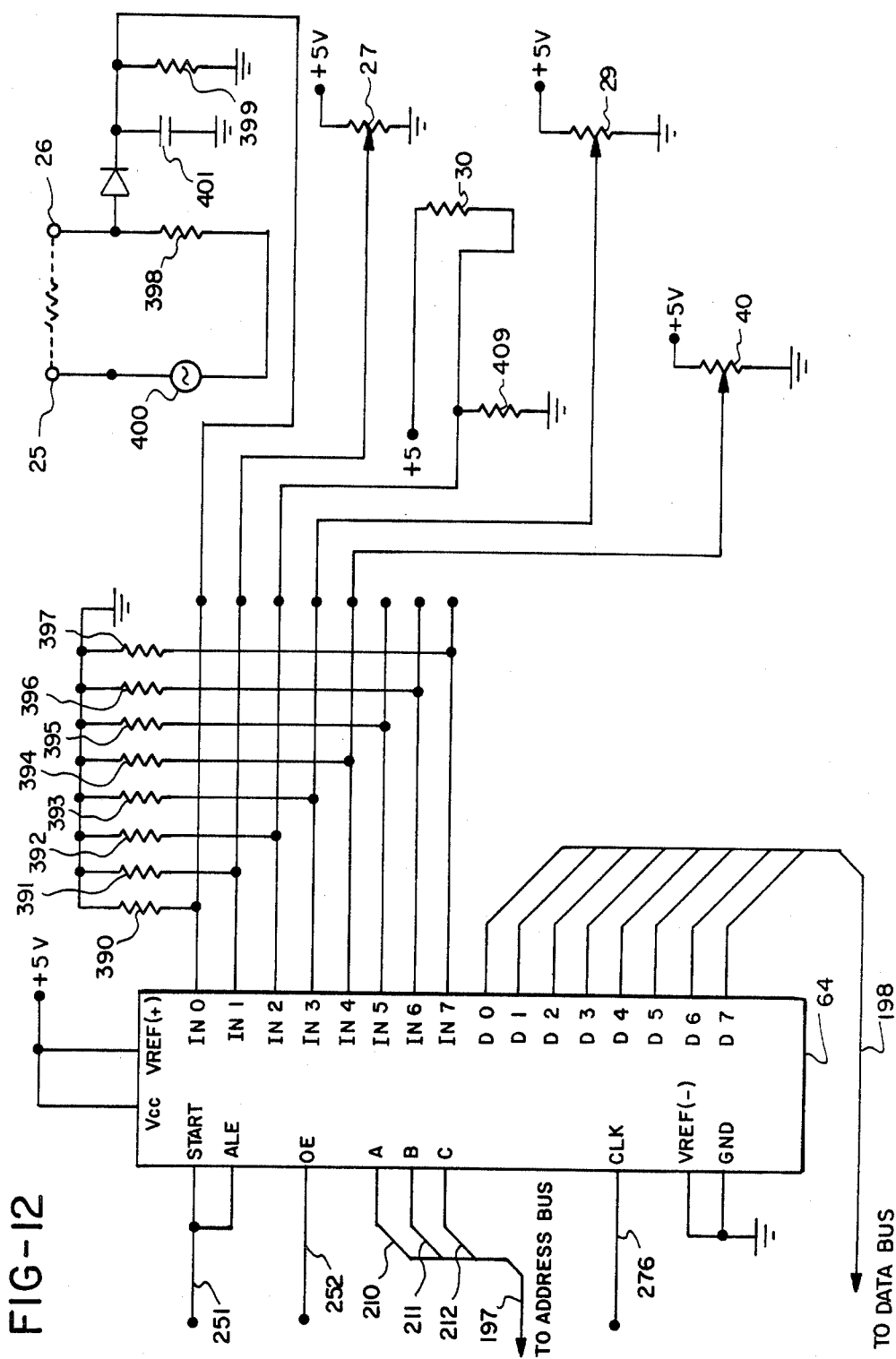
FIG. 12 is a schematic diagram of interconnections between hand control feedback sensors and an analog to digital converter.

Controller 20 includes a ten KHz oscillator 400, as illustrated in FIG. 12. Oscillator 400 may be a Signetics SE/NE 555 timer connected as shown in the manufacturer's data sheets for generation of a free running frequency of 10 KHz. When electrodes 25 and 26 are firmly adhered to the skin of the quadriplegic person, then a current of approximately one milliampere is delivered by oscillator 400 through a resistor 398 and across the skin bridging the two electrodes. This current flow creates a potential drop which is sensed by controller 20. If either of electrodes 25 or 26 breaks loose from the skin (approximately 5000 ohms) of the wearer, then a potential change is signaled to controller 20. This results in generation of an error signal which terminates the stimulation of the hand.

Continuing with the description of FIG. 2, cuff 22 comprises a series of electrodes 31, each attached to a lead wire 41 woven into the fabric of the cuff. Lead wires 41 extend toward a connector 32 mating with another connector (not illustrated) for connection to controller 20. Cuff 22 may comprise 18 electrodes 31 arranged in three groups of six electrodes each. One group of electrodes stimulates the hand flexors, another group stimulates the thumb flexors and the third stimulates the wrist extensors. The precise placement for the electrodes must be tailored to fit the particular individual. Thus the fabrication of cuff 22 must be preceded by a fitting procedure wherein electrodes are placed on the skin of the subject above the muscles to be stimulated and then moved slightly back and forth for production of maximum stimulation effect. Reference may be made to FIG. 6 for the approximate locations of a group of electrodes for stimulating the hand flexors. Once the optimum locations have been identified, a pattern is made from which cuff 22 is produced.

Electrodes 31 may be MEDTRONIC Model 3795 electrodes sold by Medtronic, Inc. of Minneapolis, Minn. A zipper 33 secures cuff 22 firmly about the forearm of the wearer, thereby assuring that electrodes 31 are accurately secured in place. A small tattoo may be placed on the arm of the quadriplegic person for use in aligning the cuff.

Glove 23 includes a length sensing arrangement and a pressure sensor for providing feedback signals to controller 20. If the quadriplegic person has any feeling in his hand, then glove 23 is not required. In that case the person's sensory system provides the required feedback to indicate when a proper degree of grasping pressure has been stimulated. At that point the shoulder postion is maintained. Thereafter, the hand is opened by backward movement of the shoulder. It will be noted that the shoulder which operates the stimulation system is that shoulder which is opposite the hand being stimulated.

For quadriplegics who do not have any feeling in their hands, glove 23 provides a most useful function. In one mode of operation glove 23 provides a closure feedback signal generated by a length sensing arrangement comprising linear potentiometer 29, a sliding wire 42 and a piece of adhesive tape 82 for securing wire 42 in place. As the hand closes into a grasping posture under control of the stimulation system, the wire 42 is extended thereby causing generation of a corresponding output potential from the potentiometer 29. Potentiometer 29 may be a linear potentiometer of the same type as potentiometer 27. Alternatively, the illustrated length sensing arrangement may be replaced by a simple strip of carbon elastomer material available from the University of Glasgow, Glasgow, Scotland. This material readily elongates to accommodate the closure of the hand which is wearing the glove. As the material stretches, its electrical resistance changes, and this is easily sensed by a simple resistance measuring circuit.

Figure 3:
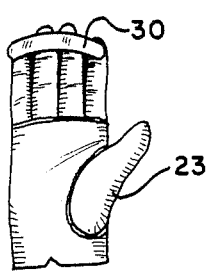
FIG. 3 is an illustration of a glove with a pressure sensor mounted thereon.

Pressure sensor 30 may be utilized for providing a feedback signal as an alternative to the above-mentioned length sensing arrangement. Pressure sensor 30 preferably is a carbon elastomer material of the type described above. A strip of such material may be secured to glove 23 as best illustrated in FIG. 3. Alternatively, pressure sensor 30 may comprise a piezoelectric crystal or other known arrangement for pressure sensing applications.

Figure 4:
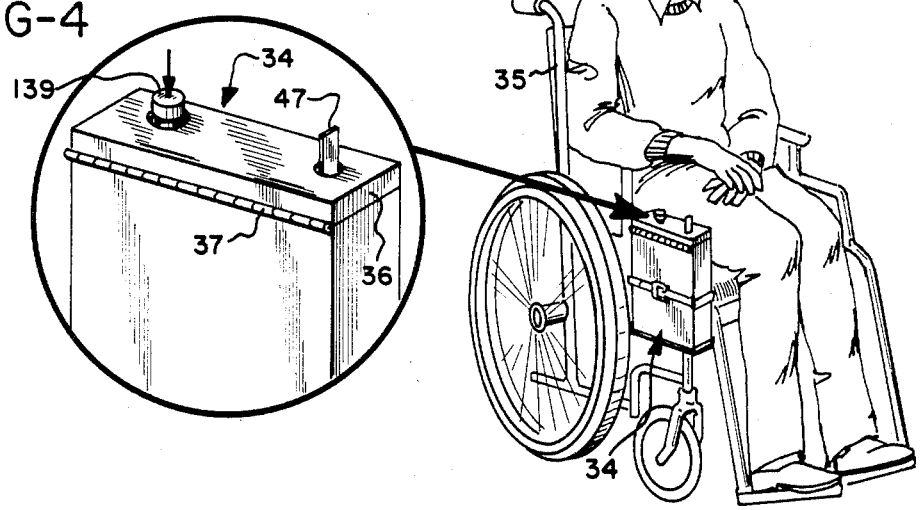
FIG. 4 illustrates a hand control system mounted on a wheelchair.
Figure 5:
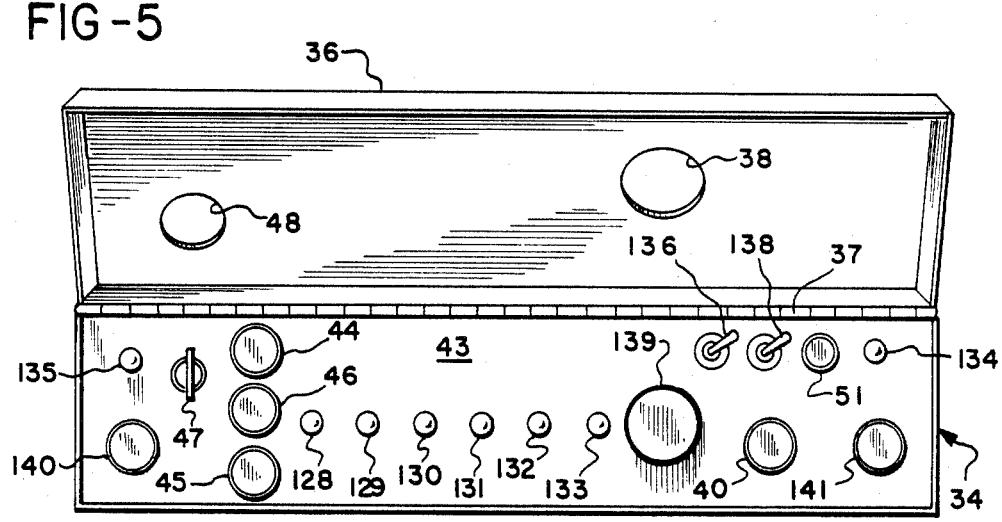
FIG. 5 is a pictorial drawing of a control panel for a hand control system.

Controller 20 may be mounted within a portable box 34 which may be fastened bo a wheelchair 35 as illustrated in FIG. 4. Box 35 may be equipped with a cover 36 secured thereto by a hinge 37. Cover 36 is provided with a pair of apertures 38 and 48 as best illustrated in FIG. 5. A reset button 139 and a stimulator power switch 48 are mounted on a control panel 43 for extending through apertures 38 and 48 respectively when the cover 36 is closed. The various switches on control panel 43 are set up once daily for programming controller 20. Thereafter, cover 36 is closed, and the quadriplegic person may engage in a day's activities utilizing the system. Reset button 139 permits immediate termination of muscle stimulation as desired by the user for any reason. Stimulator power switch 48 is provided for shutting off power to the stimulator circuits without powering down the computer portion of controller 20. This enables power conservation during relatively long periods of inactivity without requiring reprogramming of the computer.

Control panel 43 also includes a main power switch 51, which controls all power to the system, a pair of feedback designation switches 136 and 138, control knobs for four potentiometers 40, 44, 45 and 46 and a pair of programming pusbuttons 140 and 141. During the daily programming routine potentiometers 44, 45 and 46 are adjusted to produce threshold stimulation of the hand flexors, thumb flexors and wrist extensors respectively when a predetermined calibration signal is generated by the computer. Also during the programming routine potentiometer 40 is adjusted for limiting the maximum stimulation voltage to that value which just begins to produce physical discomfort. One or the other of switches 136 or 138 may be thrown to designate a feedback routine. Switch 136 selects pressure feedback while switch 138 selects length feedback.

Control panel 43 additionally includes eight light emitting diodes 128 through 134. The diodes light up to lead the user through a programming routine. LED 128 indicates that power is on and that the system is inactive. LED 129 calls for adjustment of potentiometers 44 through 46 to set the stimulation threshold, while LED 130 directs the user to adjust potentiometer 40 for setting the maximum stimulation voltage. LED 131 signals that it is time for shoulder movement to adjust the zero setting. LED 132 indicates that power is on, and LED 133 indicates that the system is programmed and active.

All controls on control panel 43 are designed for manipulation by a quadriplegic person. Following each control setting during the programming sequence one or the other of push buttons 140 or 141 must be depressed. The correct push buttons are indicated by LEDs 135 and 134 respectively. The system provides two such pushbuttons at opposite ends of the control panel to accommodate the lack of dexterity of a quadraplegic person. Activation of the push buttons alternates from left to right.

Figure 13:
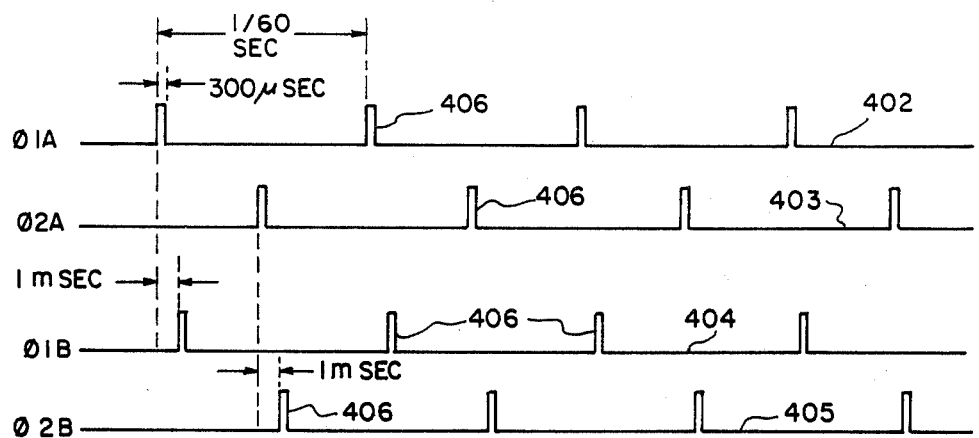
FIG. 13 is a timing diagram for four stimulation signals.

Referring now to FIG. 6, a typical placement of a group of six stimulating electrodes will be observed. The group comprises a first set of three electrodes, designated 74a through 74c and a second set designated 75a through 75c. All six electrodes of the general type designated by the reference numeral 31 of FIG. 2. Electrodes 74a, 74b and 74c are excited by a series of alternating pulses of electrical energy generated in the manner described in Petrofsky et al U.S. Application Ser. No. 417,934, filed Sept. 14, 1982. Accordingly, electrode 74c is connected to a high voltage ground while electrodes 74a and 74b are connected to pulsed sources of electrical potential. In a typical operation pulses are applied in alternating fashion, first across the electrode pair 74a–74c and then across the electrode pair 74b–74c. These alternating pulses are each applied at a frequency of about 60 Hz, and the pulses are of about 300 microseconds duration, all as taught in the Petrofsky et al application. The circuitry as hereinafter described in detail supplements the prior art electrode arrangement by adding a second set of three electrodes for cooperative excitation. Thus electrode 75c is connected to a high voltage ground while electrodes 75a and 75b are connected to sources of pulsed potential. The driving circuitry for electrodes 75a through 75c is identical to the driving circuitry for electrodes 74a through 74c. The operation of those circuits is likewise identical except for the fact that there is a phase shift between the two pairs of signals. The circuitry as hereinafter described provides a phase delay which may be adjusted anywhere in the range between about 100 microseconds and slightly over one millisecond, but a delay of about one millisecond is preferred. FIG. 13 illustrates waveforms for the signals which result.

FIG. 13 illustrates four waveforms 402 through 405 generated in response to stimulation clock signals hereinafter referred to as $\phi_{1A}$, $\phi_{2A}$, $\phi_{1B}$ and $\phi_{2B}$ respectively. The signal illustrated by waveforms 402 is applied across the electrode pair 74a–74c while the signal represented by the waveforms 403 appears across the electrode pair 74b–74c. Each waveforms comprises a series of 300 microsecond pulses 406 generated at a frequency of about 60 Hz. The pulses in waveforms 402 and 403 are alternated, as taught by the prior art.

Waveforms 404 and 405 represent stimulation signals occurring across electrode pairs 75a–75c and 75b–75c respectively. Waveforms 404 and 405 are identical to waveforms 402 and 403 that are shifted relative thereto so as to have a phase delay preferably in the amount of about one millisecond.

FIG. 6a is a cross section across the forearm of a quadriplegic person taken along lines 6a—6a of FIG. 6. The figure illustrates two electrodes 74b and 75b placed on the surface of the skin just above a mass of muscular tissue which may be the flexor digitorum sublimis and flexor digitorum superficialis manus muscle groups as represented by the reference numeral 80. Below those muscle groups lies the flexor digitorum profundus manus muscle group represented by the reference numeral 81. The latter muscle group controls hand flexure. The hand control system as described herein stimulates the flexor digitorum profundus manus muscle group without stimulating the muscle groups thereabove. The side-by-side placement of electrode groups having phase displaced signals applied thereto is believed to provide a focusing effect which is sensed by the deep muscles but not by the superficial muscles. This effect is enhanced by adjusting the stimulation voltage levels somewhat downwardly to a point where a single electrode set such as the set 74a through 74c is unable to stimulate the superficial muscles.

FIG. 7 presents a block diagram of the entire hand control system. That figure illustrates the six above-described electrode terminals 74a through 74c and 75a through 75c connected by lead lines 41 to a hand stimulating circuit 71. Similarly, a second group of six electrodes 76a through 76c and 77a through 77c are connected to a thumb stimulating circuit 72, while a third group of six electrodes 78a through 78c and 79a through 79c are connected to an extensor stimulating circuit 73. Electrodes 76a through 76c and 77a through 77c stimulate thumb flexing by stimulation of the relatively deep adductor pollicis muscle group without stimulation of superficial muscles thereabove. Electrodes 78a through 78c and 79a through 79c produce opening of the hand by stimulation of the extensor carpi ulnaris muscle group. This is also a relatively deep muscle group which must be stimulated without stimulation of overlying superficial muscles. All in all the hand control system utilizes 18 stimulation electrodes arranged in three groups of electrodes, each comprising two sets of three electrodes operating in a functionally similar manner.

FIG. 7 illustrates shoulder sensor 21, length sensor 29 and pressure sensor 30, the functions of which have been described above. Output signals from those sensors are applied, together with a signal from a potentiometer 40, to an analog to digital converter 64. Digitized output signals from analog to digital converter 64 are applied to computer 60 which produces three digital output signals representing the amplitude of the desired stimulation for the hand flexors, thumb flexors, and wrist extensors. Those three signals are applied to digital to analog converters 61 through 63 which generate analog signals for application to stimulation circuits 71 through 73 respectively. Stimulation circuits 71 through 73 are of identical construction and all receive clock signals from a stimulation clock 65. Stimulation clock 65 is responsible for the timing of the signals described above in connection with FIG. 13. The amplitudes of the pulses illustrated in that figure are controlled by the output signals from computer 60.

Figure 8A:
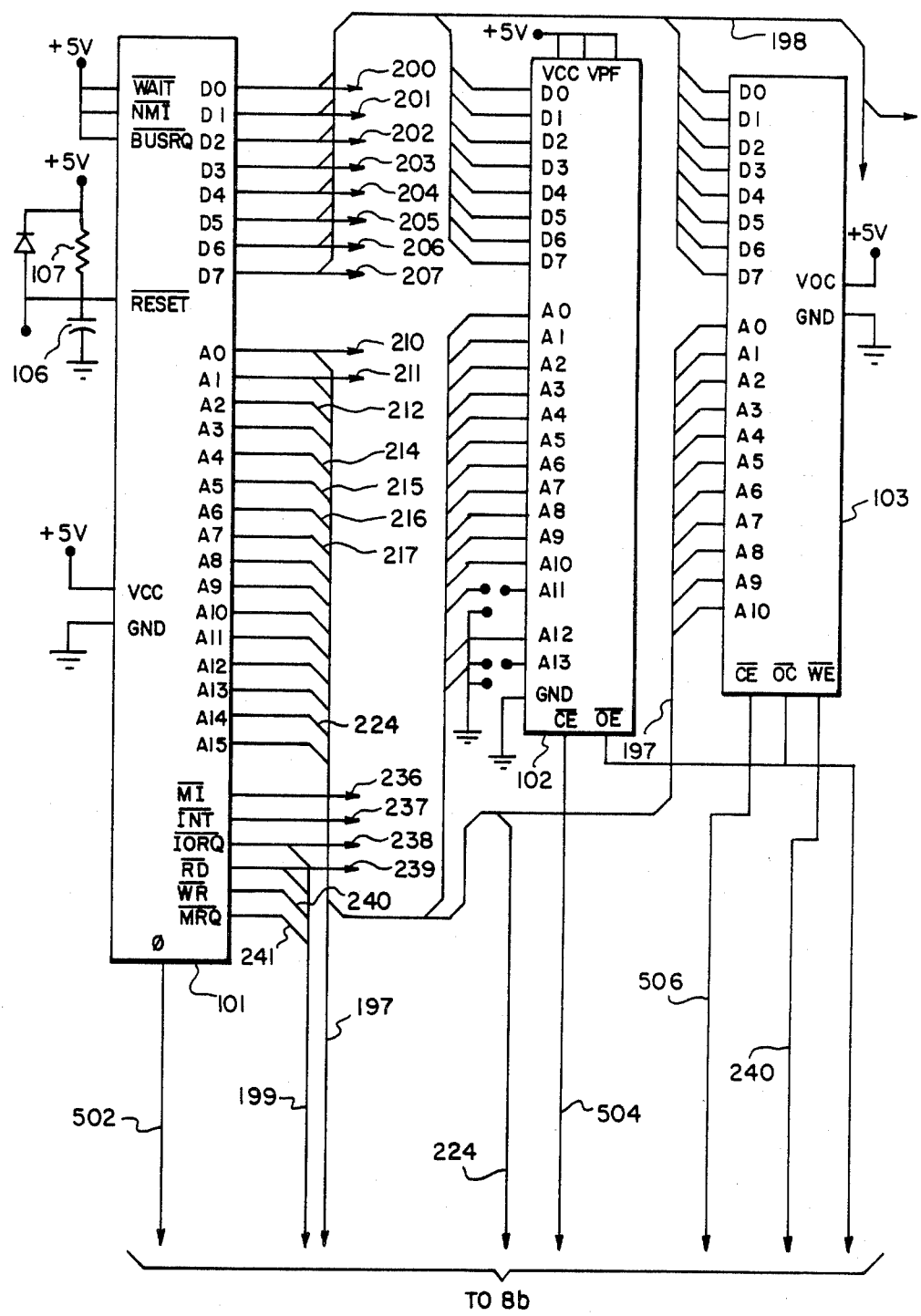
Figure 9:
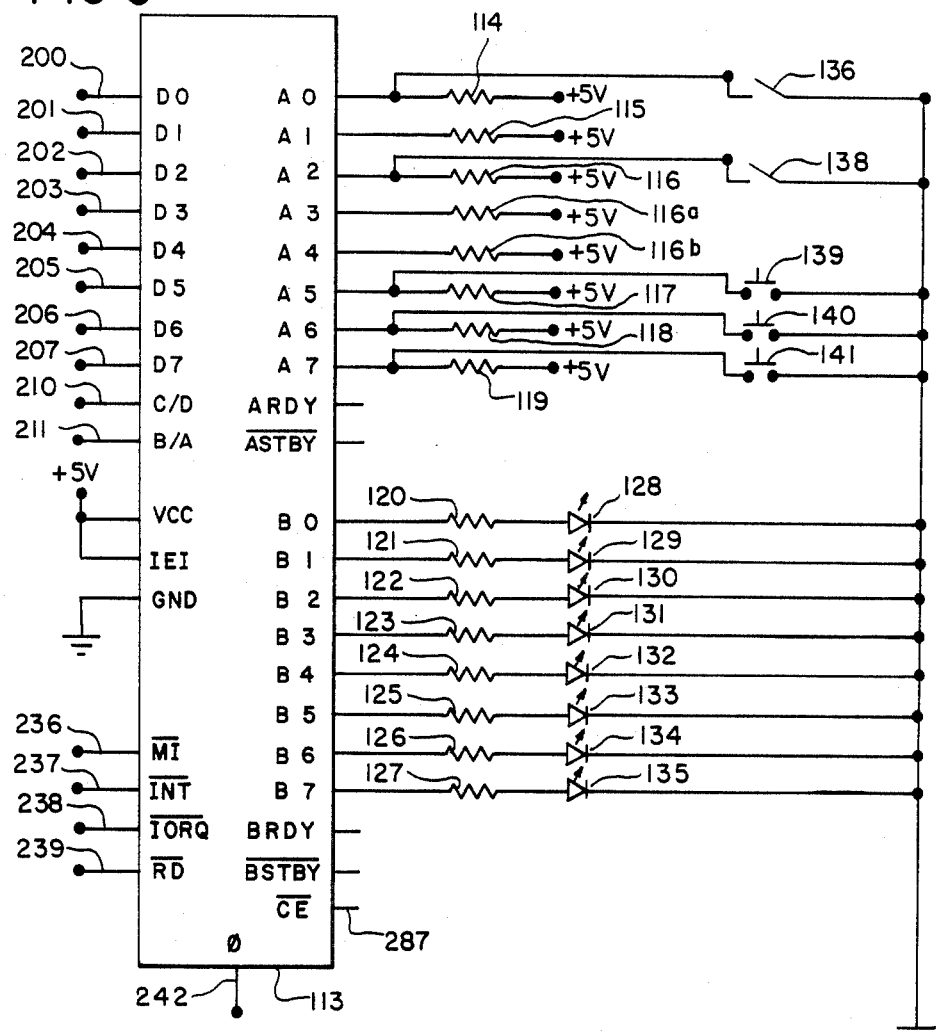
FIG. 9 is a schematic diagram of a parallel input, out port for interfacing the computer components of FIG. 8 with a control panel.

FIGS. 8a, 8b, and 9 collectively illustrate the components comprising computer 60. The major components as illustrated therein are a Z80 microprocessor 101, an EPROM 102, a read/write memory 103, a decoder/demultiplexor 104, a J-K flip-flop 105, a two MHz crystal oscillator 108 and a Z80-PIO parallel port 113. Table I presents detailed data for above components as well as other components illustrated in FIGS. 8a through 12.

TABLE I

| Ref. No | Component Data Description |
|---|---|
| 25 | ECG electrode 01-3330 (NDM Corp.) |
| 26 | ECG electrode 01-3330 (NDM Corp.) |
| 27 | 10K Ω shoulder pot. |
| 29 | 10K Ω length pot. |
| 30 | 10K Ω to 15K Ω variable resistance pressure sensor |
| 31 | Stimulation Electrode MEDTRONIC 3795 |
| 40 | 10K Ω |
| 44 | 5K Ω |
| 45 | 5K Ω |
| 46 | 5K Ω |
| 61 | DAC 0832 D,A converter (National Semiconductor) |
| 62 | DAC 0832 D,A converter (National Semiconductor) |
| 63 | DAC 0832 D,A converter (National Semiconductor) |
| 64 | ADC 0808 A,D converter (National Semiconductor) |
| 101 | Z80 microprocessor (Zilog, Inc.) |
| 102 | 2716 EPROM (Zilog) |
| 103 | 6116 Read,Write Memory (Hitachi) |
| 104 | SN74LS138 Decoder, Demultiplexer (Texas Instruments) |
| 105 | SN74LS73 flip-flop (Texas Instruments) |
| 106 | 68 μf |
| 107 | 10K Ω |
| 108 | 2 MHz oscillator |
| 109 | 0.1 μf |
| 110 | 0.1 μf |
| 111 | 0.1 μf |
| 112 | 0.1 μf |
| 113 | Z80-PIO parallel I,O port (Zilog, Inc.) |
| 114–119 | 10K Ω |
| 120–127 | 150 Ω |
| 305–312 | 2N3904 |
| 313–316 | 2SC1308 |
| 321–324 | 470 Ω |
| 329–332 | 470 Ω |
| 333–336 | 1K Ω |
| 337–340 | 100 Ω |
| 325–328 | 10K Ω |
| 333,336 | 1K Ω |
| 337–340 | 100 Ω |
| 350–356 | SE,NE 555 (Signetics) |
| 360, 361 | 100K Ω |
| 362 | 0.1 μf |
| 363 | 0.001 μf |
| 364, 365 | 10K Ω |
| 366 | .001 μf |
| 357 | 2N3904 |
| 367 | 22K Ω |
| 368 | 10K Ω |
| 369 | 0.1 μf |
| 370 | .001 μf |
| 370a | 10K Ω |
| 371 | 10K Ω |
| 372 | 10K Ω |
| 373 | 0.1 μf |
| 374, 375 | 22K Ω |
| 376 | 10K Ω |
| 377 | 0.1 μf |
| 378–380 | 10K Ω |
| 381 | 0.1 μf |
| 382 | 10K Ω |
| 383 | 22K Ω |
| 384 | 0.001 μf |
| 385 | 0.1 μf |
| 386, 387 | 0.001 μf |
| 388 | 10K Ω |
| 389 | 0.1 μf |
| 389a | 22K Ω |

TABLE I-continued

| Ref. No | Component Data Description |
|---|---|
| 390–397 | 100K Ω |
| 398 | 10K Ω |
| 399 | 100K Ω |
| 400 | 10KHz oscillator |
| 401 | 0.1 μf |
| 409 | 1K Ω |

Microprocessor 101 is connected to eight data lines 200 through 207 collectively forming a data bus identified by the reference numeral 198. Microprocessor 101 also has 16 address lines which collectively form an address bus 197. Two of these address lines, lines 210 and 211 are connected to the C/D and B/A terminals of parallel port 113. A HI signal on line 210 conditions parallel port 113 for organization of its internal registers in accordance with data applied to data terminals D0 through D7. This feature is utilized to set up parallel port 113 for reception of input data at terminals A0 through A7 and transmission of output data at terminals B0 through B7. A LO signal on line 210 conditions parallel port 113 to connect data terminals D0 through D7 for communication on a selective basis with either of terminal set A0 through A7 or B0 through B7 depending upon the state of the signal on line 211. A HI signal on line 211 selects B terminal communication while a LO signal selects A terminal communication.

When the A terminals of parallel port 113 are selected, then upon reception of a chip select signal on line 287, switches 136, 138, 139, 140 and 141 are read, and a corresponding eight-bit data word is relayed to the data terminals for transmission to microprocessor 101 on data lines 200 through 207. Alternatively, selection of the B terminals causes the bits in a data word from microprocessor 101 to produce illumination of corresponding ones of light emitting diodes 128 through 135. This operation is controlled by the assembly level instructions "OUT LIGHTS" and "IN SWITCHES". The entire program for controlling operation of microprocessor 101 is stored in memory units 102 and 103. That program is listed below in Table II.

Crystal oscillator 108 provides a clock for operation of microprocessor 101 and flip-flop 105. A clock signal is also provided on line 242 for application to parallel port 113. Also as illustrated in FIGS. 8a, 8b and 9, parallel port 113 is connected to lines 236 through 239 from microprocessor 101 for purposes of normal operating control.

Decoder/demultiplexor 104 is connected via lines 214 through 217 to address terminals A4 through A7 of microprocessor 101. This provides a four-bit address code for activation of one of eight output lines 280 through 287. Line 287 is connected to the chip selection terminal of parallel port 113 to cause the above-described operation of the parallel port upon generation of hexadecimal address F2 by microprocessor 101. Addresses 9O, AO and BO cause activation of decoder output lines 281, 282 and 283 for selection of D/A converters 61, 62 and 63 respectively (hand, thumb and extensor stimulation). Decoder output lines 280, 284 and 285 are not utilized.

Flip-flop 105 produces output pulses on line 276 for use as a clock by A/D converter 64. As illustrated by a small inset on FIG. 8b all power supplies are filtered through a series of 0.1 microfara capacitors to eliminate system noise.

Microprocessor 101 also selects feedback signals for transmission by A/D converter 64. This selection is made by means of a three-bit address code on lines 210 through 212 of address bus 197. The hexadecimal code E1 selects the shoulder sensor, while E2 selects the pressure sensor and E3 selects the length sensor. The code E4 selects potentiometer 40 which is appropriately adjusted during system programming for setting of the maximum permitted stimulation level. The hexadecimal code E0 selects the analog input which indicates satisfactory attachment of the shoulder sensor to the skin of the wearer. An address code of F0 is directly applied to parallel port 113 for chip selection, as described above.

Figure 10:
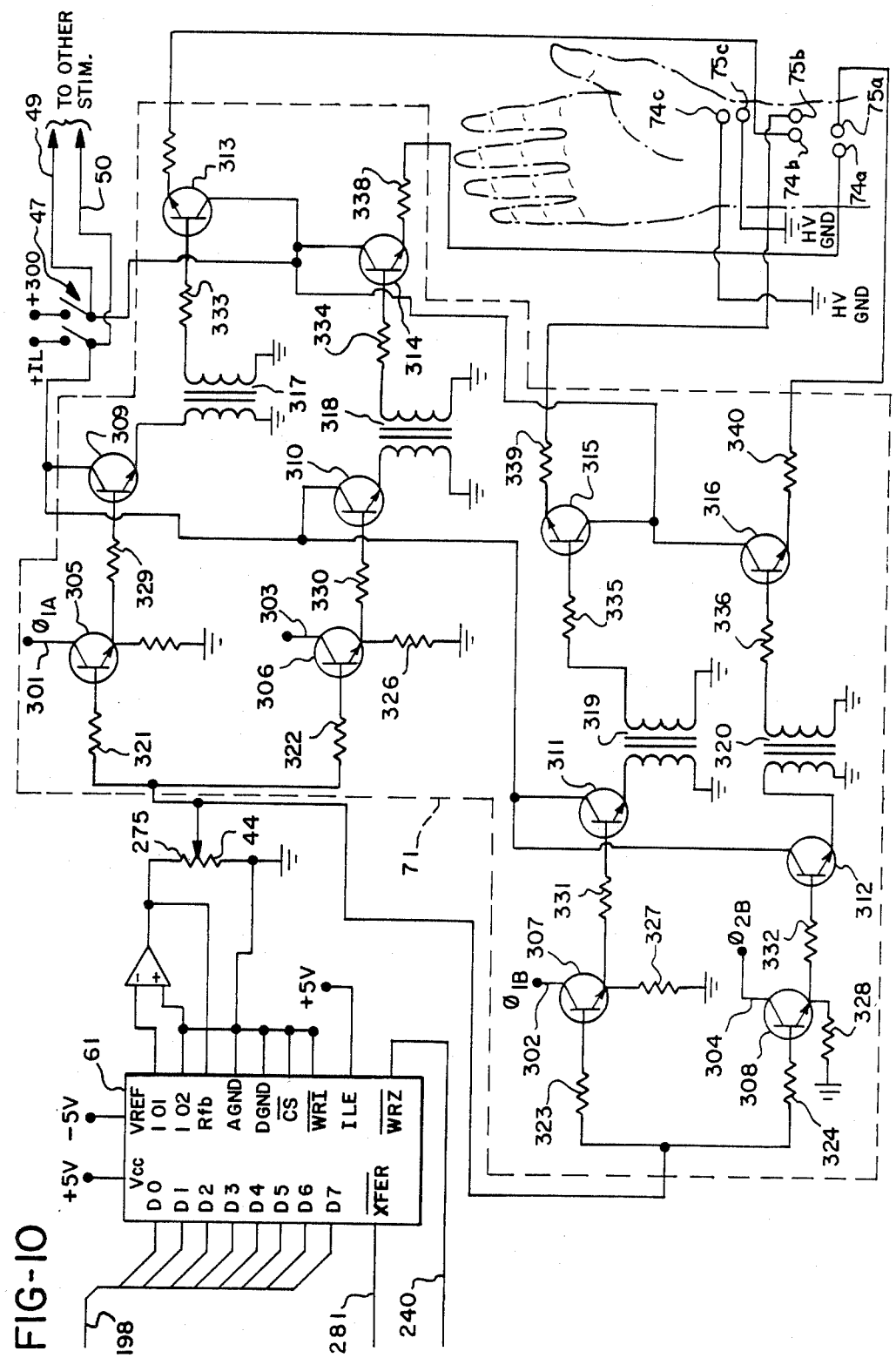
FIG. 10 is a schematic illustration of a stimulation channel including a digital to analog converter and a stimulation driver.

As noted above, computer 60 generates digital codes on data bus 198 which represent desired stimulation amplitudes for the three muscle groups to be stimulated. Those codes are applied to D/A converters 61 through 63, as selected by decoder 104. FIG. 10 illustrates the details of one stimulation channel including D/A converter 61, hand flexor stimulator 71 and stimulation electrodes 74a through 75c. The circuits for stimulating the thumb and the extensor are similar and are not illustrated in detail.

Referring now to FIG. 10, D/A converter 61 is selected for operation by a selection signal appearing on line 281 from the Y1 terminal of decoder 104 (address code 90 hex). A write control signal is also received from microprocessor 101 via line 240. Stimulation amplitude codes are applied by data bus 198 to the data terminals of D/A converter 61, and analog representations thereof appear across potentiometer 275. Potentiometer 44 and similar potentiometers (44,46) at the output sides of D/A converters 62 and 63 are individually adjusted as part of a calibration procedure performed on a daily basis for the particular quadriplegic person utilizing the equipment. Calibration is carried out by placing the hexadecimal number 40 into the accumulator of microprocessor 101 and outputting that number to all three muscle control channels. The potentiometers are adjusted during reception of that particular driving signal so as to produce a slight muscle twitch indicating application of a threshold stimulation voltage.

Output signals from potentiometer 44 are applied to the base terminals of transistors 305, 306, 307 and 308. Concomitantly timing pulses from stimulation clock 65 are applied to lines 301, 303, 302 and 304 for application to the collector terminals of transistors 305, 306, 307 and 308 respectively. As a result thereof, transistors 305 through 308 generate emitter currents across resistors 329 through 332 for application to the base terminals of transistors 309 through 312. Transistors 309 through 312 generate a series of pulses across the primary windings of transformers 317 through 320. The signals so applied across the primary windings of transformers 317 through 320 have the general form illustrated in FIG. 13. The signals so produced comprise a series of pulses having maximum amplitudes which may range between 0 and 12 volts. These signals across the primary windings of transformers 317 through 320 cause production of low current, high voltage pulses ranging from 0 to 255 volts across the secondary windings of the transformers. The second windings of the transformers have one side grounded to a high voltage ground which is different from the ground utilized for the primary windings thereof. The output pulses from the secondary windings are thereby RF isolated to maintain the safety of the quadriplegic person.

Output voltages from transformers 317 through 320 are applied to the base terminals of transistors 313 through 316 respectively. Transistors 313 through 316 provide a current gain so as to have high current, high voltage and low duty cycle pulses available for application across the pairs of electrode terminals which are serviced thereby.

Figure 11:
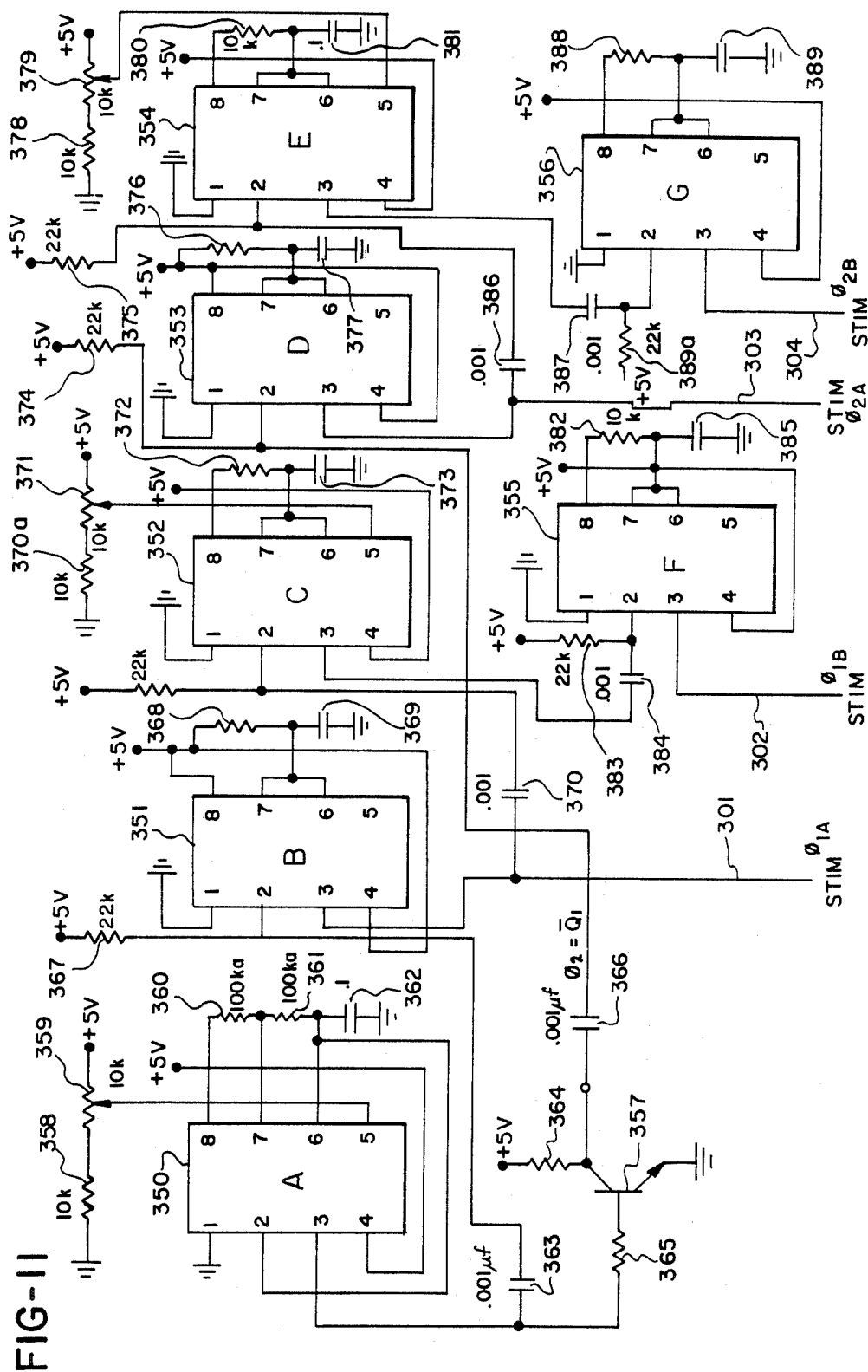
FIG. 11 is a schematic diagram of a stimulation clock.

FIG. 11 illustrates the details of stimulation clock 65. As illustrated in FIG. 11, the circuit comprises seven SE,NE555 timers 350 through 356. Timer 350 is the clock oscillator for the circuit. Pin 5 of timer 350 is attached to a potentiometer arrangement including two 10K resistors. The potentiometer is adjusted for control of the basic stimulation frequency which may run between 20 and 60 Hz, 60 Hz being preferred.

The output of timer 350 is inverted by transistor 357 to provide a clock phase I and a clock phase II signal. The phase I and phase II signals excite timers 351 and 353 respectively. These timers are set up as one shot multi-vibrators in contrast to the free running operation of timer 350. Timers 351 and 353 provide output pulses which are 180° out of phase. Resistors 368 and 376 and capacitors 369 and 377 cause those pulses to have a pulse width of 300 microseconds. These pulses are applied to lines 301 and 303 for timing control of waveforms 402 and 403 of FIG. 13.

The pulses applied to lines 301 and 303 are also applied to timers 352 and 354 respectively. These latter two timers are delay timers having terminals No. 5 thereof connected to potentiometer arrangements as illustrated in FIG. 11. Depending upon the setting of those potentiometers, timers 353 and 354 are able to produce delays ranging from about 180 microseconds to just over one millisecond. Output signals from timers 352 and 354 trigger timers 355 and 356 respectively, which are set up as one shot multi-vibrators. Timers 355 and 356 produce output signals on lines 302 and 304 which time the generation of the pulses illustrated by waveforms 404 and 405 of FIG. 13.

FIG. 12 illustrates the details of electrical connections for A,D converter 64. That converter has five input lines connected for receiving five different analog signals, as above described. Input signals on lines 210 through 212 of address bus 197 select a desired analog signal for digitizing. The digitized signal is transmitted to data bus 198 for relay to microprocessor 101.

The program listing, as set forth in Table II, is written in 8080 assembly language. The program, when assembled, will run on a Z80 microprocessor. The program includes a common stem program, a pressure sub-routine and a length sub-routine. The pressure or length sub-routines are selected by activating one or the other of switches 136 or 138 on control panel 43. These switches are checked at program lines 304 and 307, and sub-routine entries are made at those points as appropriate.

For all operating modes the program requires threshold settings of potentiometers 44–46, as described above. This sets the gain of stimulators 71–73 to produce threshold stimulation for a stimulation command of 40 (hexadecimal). This is followed by a setting of potentiometer 40 which generates analog input signals effectively simulating shoulder movement. During this part of the programming a series of settings of potentiometer 40 are made, read and digitized. A hexadecimal value of 40 (threshold set) is added to each digitized result, and the sum is output for generation of a stimulation signal. Settings of potentiometer 40 are gradually increased until the subject feels that the stimulation level is uncomfortable. The computer stores the digitized value of the analog input which produces such a condition and thereafter treats that value as a maximum shoulder command signal. Shoulder commands which exceed the maximum value, so determined, are ignored. This is a safety procedure to prevent pain or injury to the subject.

After the setting of the potentiometers has been completed the program enters the routine beginning at line 268, wherein the subject calibrates the zero position of the shoulder sensor. During this routine the quadriplegic person moves his shoulder back and forth until a comfortable middle position has been achieved. At this point push button 141 is depressed to signal the computer that this position is to be used as a zero point. When the shoulder moves back from this position the hand opens. If it is moved in the forward direction the hand will close. The greater the forward movement, the greater the hand closure. This provides full open-loop control of the hand with feedback being provided by the human eye and the nerves in the fingers.

Following zeroing of the shoulder sensor the program checks to ascertain the position of switches 136 and 138 in order to determine whether or not the open loop hand control routine should be supplanted by closed loop control using feedback signals from length sensor 23 or pressure sensor 30. The sub-routines for pressure and length feedback commence at line numbers 409 and 461 respectively. In these closed loop routines the signal from the shoulder sensor is subtracted from the feedback signal to develop an error signal (program lines 419 and 472). If the error signal is negative, then the stimulation voltage is increased. Thus the shoulder is used to generate pressure or length commands.

As described above the computer periodically checks for attachment of shoulder sensor 21 to the skin of the subject. This check is made at line 331. If that check indicates that the sensor is loose, then the program jumps into an error routine beginning at line 357.

While the method herein described, and the form of apparatus for carrying this method into effect, constitute preferred embodiments of this invention, it is to be understood that the invention is not limited to this precise method and form of apparatus, and that changes may be made in either without departing from the scope of the invention, which is defined in the appended claims.

TABLE II

```
 1:
 2:
 3:
 4:
 5:
 6:
 7:
 8:
 9:         ;*** PARALLEL OUTPUT PORT BIT
            DESIGNATIONS ***
10:
11:         ;ALL BITS ARE ACTIVE HIGH
12:
13:         ;BIT 0=SYSTEM INACTIVE
14:         ;BIT 1-THRESHOLD SET
15:         ;BIT 2=MAX VOLTAGE SET
16:         ;BIT 3-ZERO SENSOR SET
17:         ;BIT 4=SYSTEM ON
18:         ;BIT 5=MEASURING
19:         ;BIT 6=RIGHT SWITCH
20:         ;BIT 7=LEFT SWITCH
21:
22:
23:         ;*** PARALLEL INPUT PORT BIT
            DESIGNATIONS***
24:
25:         ;ALL SWITCHES ACTIVE LOW
26:
27:
28:         ;BIT 0 = FEEDBACK CONTROL PRESSURE
29:         ;BIT 2 = FEEDBACK CONTROL LENGTH
30:         ;BIT 5 = RESET FOR COMPUTER
31:         ;BIT 6 = LEFT BUTTON
32:         ;BIT 7 = RIGHT BUTTON
33:
```

```
 34:                    ;*** INPUT PORT NUMBERS ***
 35:
 36:                    ;0E0H = SENSOR CHECK
 37:                    ;0E1H = SHOULDER SENSOR
 38:                    ;0E2H = PRESSURE SENSOR
 39:                    ;0E3H = LENGTH SENSOR
 40:                    ;0E4H = ANALOG INPUT
 41:                    ;0F0H = 8-BIT PARALLEL INPUT PORT
 42:
 43:                    ;*** OUTPUT PORT NUMBERS ***
 44:
 45:                    ;090H = HAND CONTROL
 46:                    ;0A0H = THUMB CONTROL
 47:                    ;0B0H = EXTENSOR CONTROL
 48:                    ;0F2H = 8-BIT PARALLEL OUTPUT PORT
                         (LED'S)
 49:
 50:
 51:                    ; REGISTER ALLOCATION
 52:
 53:                    ;       L=HAND FLEX MAX
 54:                    ;       H=THUMB FLEX MAX
 55:                    ;       E=EXTENSOR MAX
 56:                    ;       C=SENSOR ZERO
 57:                    ;       B=TEMP STORE
 58:                    ;       D=PRESSURE OR HAND LENGTH
                                   VOLTAGE STORE
 59:
 60:
 61:
 62:
 63:  0100              START:  ORG     100H
 64:
 65:                    ;*****************************
 66:                    ;*
 67:                    ;*      INITIALIZE PORTS
 68:                    ;*
 69:                    ;*****************************
 70:
 71:  0080 =            DAC0        EQU     080H
 72:  0090 =            DAC1        EQU     090H
 73:  00A0 =            DAC2        EQU     0A0H
 74:  00B0 =            DAC3        EQU     0B0H
 75:  00C0 =            DAC4        EQU     0C0H
 76:  00D0 =            DAC5        EQU     0D0H
 77:
 78:  00E0 =            ADC0        EQU     0E0H
 79:  00E1 =            ADC1        EQU     0E1H
 80:  00E2 =            ADC2        EQU     0E2H
 81:  00E3 =            ADC3        EQU     0E3H
 82:  00E4 =            ADC4        EQU     0E4H
 83:  00E5 =            ADC5        EQU     0E5H
 84:  00E6 =            ADC6        EQU     0E6H
 85:  00E7 =            ADC7        EQU     0E7H
 86:
 87:  00F0 =            PIO$DATA$A  EQU     0F0H
 88:  00F1 =            PIO$CTRL$A  EQU     0F1H
 89:  00F2 =            PIO$DATA$B  EQU     0F2H
 90:  00F3 =            PIO$CTRL$B  EQU     0F3H
 91:
 92:  4000 =            RAM         EQU     400H
```

```
 93:  47FF =              RAM$TOP    EQU    RAM + 07FFH      ;**TOP
                                                              OF RAM**
 94:
 95:  00F2 =              LIGHTS     EQU    PIO$DATA$B
 96:  00F0 =              SWITCHES   EQU    PIO$DATA$A
 97:  00E0 =              SENSOR     EQU    ADC0
 98:  00E4 =              ANALOG     EQU    ADC4
 99:  0090 =              HAND       EQU    DAC1
100:  00A0 =              THUMB      EQU    DAC2
101:  00B0 =              EXTENSOR   EQU    DAC3
102:  00E1 =              SHOULDER   EQU    ADC1
103:  00E2 =              PRESS      EQU    ADC2
104:  00E3 =              LEN        EQU    ADC3
105:
106:  0100 F3                        DI
107:  0101 31FF47                    LXI    SP,RAM$TOP
108:
109:  0104 AF                        XRA    A                ;A = 0
110:  0105 D380                      OUT    DAC0
111:  0107 D390                      OUT    DAC1
112:  0109 D3A0                      OUT    DAC2
113:  010B D3B0                      OUT    DAC3
114:  010D D3C0                      OUT    DAC4
115:  010F D3D0                      OUT    DAC5
116:
117:  0111 3E4F                      MVI    A,4FH            ;SET PIO
                                                              PORT A
118:  0113 D3F1                      OUT    PIO$CTRL$A       ;TO
                                                              INPUT
119:
120:  0115 3E0F                      MVI    A,0FH            ;SET PIO
                                                              PORT B
121:  0117 D3F3                      OUT    PIO$CTRL$B       ;TO
                                                              OUTPUT
122:
123:  0119 FB                        EI
124:
125:                     ;******************************************
126:
127:
128:  011A 3E00  BARF               MVI    A,00
129:  011C 57                       MOV    D,A
130:  011D D390                     OUT    HAND
131:  011F D3A0                     OUT    THUMB
132:  0121 D3B0                     OUT    EXTENSOR
133:  0123 3E41                     MVI    A,41H
134:  0125 D3F2                     OUT    LIGHTS
135:  0127 DBF0  LOOP1              IN     SWITCHES
136:  0129 E620                     ANI    20H
137:  012B CA1A01                   JZ     BARF
138:  012E DBF0                     IN     SWITCHES
139:  0130 E680                     ANI    80H
140:  0132 C22701                   JNZ    LOOP1;LOOP IN RIGHT
                                                   BUTTON NOT HIT
141:  0135 3E82                     MVI    A,82H
142:  0137 D3F2                     OUT    LIGHTS;SET DISPLAY
                                                   FOR THRESHOLD
                                                   SET
143:
144:
145:            ;                   *****THRESHOLD SET*****
146:
```

```
147:   0139 DBF0      LOOP20           IN       SWITCHES
148:   013B E620                       ANI      20H
149:   013D CA1A01                     JZ       BARF
150:   0140 DBF0                       IN       SWITCHES
151:   0142 E640                       ANI      40H
152:   0144 C23901                     JNZ      LOOP20
153:   0147 3E62                       MVI      A,62H
154:   0149 D3F2                       OUT      LIGHTS
155:   014B 3E40                       MVI      A,40H;SET OUTPUT
                                                    VOLTAGE
156:   014D D390                       OUT      HAND
157:   014F D3A0                       OUT      THUMB
158:   0151 D3B0                       OUT      EXTENSOR
159:                ;****THRESHOLD  OFF****
160:
161:   0153 DBF0      LOOP2            IN       SWITCHES
162:   0155 E620                       ANI      20H
163:   0157 CA1A01                     JZ       BARF
164:   015A DBF0                       IN       SWITCHES
165:   015C E680                       ANI      80H;LEFT BUTTON HELD
                                                    DOWN FOR
                                                    THRESHOLD
166:   015E C25301                     JNZ      LOOP2
167:   0161 3E00                       MVI      A,00
168:   0163 D390                       OUT      HAND
169:   0165 D3A0                       OUT      THUMB
170:   0167 3E84                       MVI      A,84H
171:   0169 D3F2                       OUT      LIGHTS
172:
173:                ;****MAX VOLTAGE SET HAND
174:
175:   016B DBF0      LOOP3            IN       SWITCHES
176:   016D E620                       ANI      20H
177:   016F CA1A01                     JZ       BARF
178:   0172 DBF0                       IN       SWITCHES
179:   0174 E640                       ANI      40H
180:   0176 C26B01                     JNZ      LOOP3;LOOK FOR MAX
                                                    VOLTAGE SET
                                                    HAND
181:   0179 3E64                       MVI      A,64H
182:   017B D3F2                       OUT      LIGHTS;SET DISPLAY
                                                    FOR HAND MAX
183:   017D D3E4CDDE03LOOP4            OUT ANALOG  !  CALL
                                                DELAY100  !   IN
                                                ANALOG
184:   0184 C640                       ADI      40H
185:   0186 D390                       OUT      HAND
186:   0188 DBF0                       IN       SWITCHES
187:   018A E620                       ANI      20H
188:   018C CA1A01                     JZ       BARF
189:   018F DBF0                       IN       SWITCHES
190:   0191 E680                       ANI      80H
191:   0193 C27D01                     JNZ      LOOP4
192:
193:                ;**** STORE MAX HAND ****
194:
195:   0196 D3E4CDDE03                 OUT ANALOG  !   CALL
                                                DELAY100  !  IN
                                                ANALOG
196:   019D 6F                         MOV      L,A;STORE MAX
                                                    HAND  IN L
```

```
197:   019E  3E00                    MVI     A,00
198:   01A0  D390                    OUT     HAND
199:   01A2  3E84                    MVI     A,84H
200:   01A4  D3F2                    OUT     LIGHTS
201:
202:
203:                  ;**** MAX VOLTAGE SET THUMB ****
204:
205:
206:   01A6  DBF0       LOOP5        IN      SWITCHES
207:   01A8  E620                    ANI     20H
208:   01AA  CA1A01                  JZ      BARF
209:   01AD  DBF0                    IN      SWITCHES
210:   01AF  E640                    ANI     40H
211:   01B1  C2A601                  JNZ     LOOP5
212:   01B4  3E64                    MVI     A,64H
213:   01B6  D3F2                    OUT     LIGHTS
214:   01B8  D3E4CDDE03 LOOP6        OUT  ANALOG  !  CALL
                                       DELAY100  !  IN
                                       ANALOG
215:   01BF  C640                    ADI     40H
216:   01C1  D3A0                    OUT     THUMB
217:
218:
219:   01C3  DBF0                    IN      SWITCHES
220:   01C5  E620                    ANI     20H
221:   01C7  CA1A01                  JZ      BARF
222:   01CA  DBF0                    IN      SWITCHES
223:   01CC  E680                    ANI     80H
224:   01CE  C2B801                  JNZ     LOOP6
225:   01D1  D3E4CDDE03              OUT  ANALOG  !  CALL
                                       DELAY100  !  IN
                                       ANALOG
226:   01D8  67                      MOV     H,A
227:                  ;THUMB         MAX     IN      H
228:   01D9  3E00                    MVI     A,00
229:   01DB  D3A0                    OUT     THUMB
230:
231:
232:                  ;EXTENSOR              MAX
233:
234:
235:   01DD  3E84                    MVI     A,84H
236:   01DF  D3F2                    OUT     LIGHTS
237:   01E1  DBF0       LOOP310      IN      SWITCHES
238:   01E3  E620                    ANI     20H
239:   01E5  CA1A01                  JZ      BARF
240:   01E8  DBF0                    IN      SWITCHES
241:   01EA  E640                    ANI     40H
242:   01EC  C2E101                  JNZ     LOOP310
243:   01EF  3E64                    MVI     A,64H
244:   01F1  D3F2                    OUT     LIGHTS
245:   01F3  D3E4CDDE03 LOOP400      OUT  ANALOG  !  CALL
                                       DELAY100  !  IN
                                       ANALOG
246:   01FA  C640                    ADI     40H
247:   01FC  D3B0                    OUT     EXTENSOR
248:   01FE  DBF0                    IN      SWITCHES
249:   0200  E620                    ANI     20H
250:   0202  CA1A01                  JZ      BARF
251:   0205  D3E4CDDE03              OUT  ANALOG  !  CALL
                                       DELAY100  !  IN
                                       ANALOG
```

| | | | | | |
|---|---|---|---|---|---|
| 252: | 020C 5F | | MOV | E,A | |
| 253: | 020D DBF0 | | IN | SWITCHES | |
| 254: | 020F E680 | | ANI | 80H | |
| 255: | 0211 C2F301 | | JNZ | LOOP400 | |
| 256: | 0214 3E88 | | MVI | A,88H | |
| 257: | 0216 D3F2 | | OUT | LIGHTS | |
| 258: | 0218 DBF0 | LOOP7 | IN | SWITCHES | |
| 259: | 021A E620 | | ANI | 20H | |
| 260: | 021C CA1A01 | | JZ | BARF | |
| 261: | 021F DBF0 | | IN | SWITCHES | |
| 262: | 0221 E640 | | ANI | 40H | |
| 263: | 0223 C21802 | | JNZ | LOOP7 | |
| 264: | 0226 3E68 | | MVI | A,68H | |
| 265: | 0228 D3F2 | | OUT | LIGHTS;SET OUTPUT ACTIVE | |
| 266: | | | | | |
| 267: | | | | | |
| 268: | | ;**SET SENSOR ZERO** | | | |
| 269: | | | | | |
| 270: | | | | | |
| 271: | 022A DBF0 | LOOP8 | IN | SWITCHES | |
| 272: | 022C E620 | | ANI | 20H | |
| 273: | 022E CA1A01 | | JZ | BARF | |
| 274: | 0231 DBF0 | | IN | SWITCHES | |
| 275: | 0233 E680 | | ANI | 80H | |
| 276: | 0235 C22A02 | | JNZ | LOOP8 | |
| 277: | 0238 D3E1CDDE03 | | OUT SHOULDER ! CALL DELAY100 ! IN SHOULDER | | |
| 278: | 023F C600 | | ADI | 00 | |
| 279: | 0241 FAC602 | | JM | LOOP300 | |
| 280: | 0244 4F | LOOP301 | MOV | C,A | |
| 281: | | ;C REGISTER =SENSOR 0 | | | |
| 282: | | | | | |
| 283: | | | | | |
| 284: | | ;**START HAND CONTROL** | | | |
| 285: | | | | | |
| 286: | | | | | |
| 287: | 0245 3E90 | | MVI | A,90H | |
| 288: | 0247 D3F2 | | OUT | LIGHTS | |
| 289: | 0249 DBF0 | LOOP9 | IN | SWITCHES | |
| 290: | 024B E640 | | ANI | 40H | |
| 291: | 024D C24902 | | JNZ | LOOP9;CHECK FOR START WORK | |
| 292: | 0250 3E70 | | MVI | A,70H | |
| 293: | 0252 D3F2 | | OUT | LIGHTS;SET SYSTEM ACTIVE | |
| 294: | 0254 3E00 | | MVI | A,0 | |
| 295: | 0256 57 | | MOV | D,A | |
| 296: | 0257 DBF0 | LOOP10 | IN | SWITCHES ;CHECK FOR RESET | |
| 297: | 0259 E620 | | ANI | 20H | |
| 298: | 025B CA1A01 | | JZ | BARF | |
| 299: | 025E D3E1CDDE03 | | OUT SHOULDER ! CALL DELAY100 ! IN SHOULDER | | |
| 300: | 0265 91 | | SUB | C | |
| 301: | 0266 FAAA02 | | JM | LOOP201; LOOP OUT IF SENSOR NOT AT THRESHOLD | |
| 302: | 0269 47 | | MOV | B,A | |
| 303: | | ;CHECK FOR NO FEEDBACK OR FEEDBACK | | | |

```
304:   026A DBF0                    IN      SWITCHES
305:   026C E600                    ANI     1
306:   026E CA1903                  JZ      PRESSURE
307:   0271 DBF0                    IN      SWITCHES
308:   0273 E604                    ANI     4
309:   0275 CA7C03                  JZ      LENGTH  ; RETURN TO
                                                     LOOP10
                                                     AFTER
                                                     SUBROUTINE
310:                  ;TEMP         STORE   OF      OUT VOLTAGE
311:   0278 78                      MOV     A,B
312:   0279 94                      SUB     H;CHECK THUMB MAX
313:   027A F28602                  JP      LOOP11
314:   027D 78                      MOV     A,B
315:   027E C640                    ADI     40H
316:   0280 D3A0                    OUT     THUMB
317:   0282 3E00                    MVI     A,00
318:   0284 D3B0                    OUT     EXTENSOR
319:   0286 78       LOOP11         MOV     A,B
310:   0287 95                      SUB     L;CHECK HAND MAX
321:   0288 F29402                  JP      LOOP12
322:   0288 78                      MOV     A,B
323:   028C C640                    ADI     40H
324:   028E D390                    OUT     HAND
325:   0290 3E00                    MVI     A,00
326:   0292 D3B0                    OUT     EXTENSOR
327:
328:
329:                  ;****CHECK    END     HAND****
330:
331:   0294 D3E0CDDE03LOOP12        OUT SENSOR ! CALL
                                            DELAY100 ! IN
                                            SENSOR; CHECK FOR
                                            LOOSE SENSOR
332:   029B FE1E                    CPI     30
333:   029D F2CB02                  JP      ERROR; SENSOR LOOSE
334:   02A0 DBF0                    IN      SWITCHES
335:   02A2 E680                    ANI     80H
336:   02A4 C25702                  JNZ     LOOP10
337:   02A7 C31A01                  JMP     BARF
338:                  ;SET EXTENSOR AND ZERO FLEXORS
339:   02AA 3E00     LOOP201        MVI     A,00
340:   02AC D390                    OUT     HAND
341:   02AE D3A0                    OUT     THUMB
342:   02B0 57                      MOV     D,A
343:   02B1 D3E1CDDE03              OUT SHOULDER ! CALL
                                            DELAY100 ! IN
                                            SHOULDER
344:   02B8 91                      SUB     C
345:   02B9 C60A                    ADI     10
346:   02BB F25702                  JP      LOOP10
347:   02BE 7B                      MOV     A,E
348:   02BF D614                    SUI     20
349:   02C1 D3B0                    OUT     EXTENSOR
350:   02C3 C35702                  JMP     LOOP10
351:
352:   02C6 3E00     LOOP300        MVI     A,00
353:   02C8 C34402                  JMP     LOOP301
354:
355:
356:
```

```
357:                    ;    ****ERROR   ELECTRODE   LOOSE****
358:
359:
360:   02CB  3E00    ERROR       MVI     A,00
361:   02CD  D370                OUT     112
362:   02CF  D390                OUT     HAND
363:   02D1  D3A0                OUT     THUMB
364:   02D3  D3B0                OUT     EXTENSOR
365:   02D5  5F                  MOV     E,A
366:   02D6  3EFF                MVI     A,255
367:   02D8  D3F2                OUT     LIGHTS
368:   02DA  DBF0                IN      SWITCHES
369:   02DC  E620                ANI     20H
370:   02DE  CA1A01              JZ      BARF
371:   02E1  3E00                MVI     A,00
372:
373:               ;FLASH
374:
375:   02E3  C601    ERROR1      ADI     01
376:   02E5  C2E302              JNZ     ERROR1
377:   02E8  7B                  MOV     A,E
378:   02E9  C601                ADI     01
379:   02EB  5F                  MOV     E,A
380:   02EC  C2E302              JNZ     ERROR1
381:   02EF  3E00    ERROR2      MVI     A,00
382:   02F1  5F                  MOV     E,A
383:   02F2  3E00                MVI     A,00
384:   02F4  D3F2                OUT     LIGHTS
385:   02F6  DBF0                IN      SWITCHES
386:   02F8  E620                ANI     20H
387:   02FA  CA1A01              JZ      BARF
388:   02FD  3E00                MVI     A,00
389:   02FF  C601    ERROR3      ADI     01
390:   0301  00                  NOP
391:   0302  00                  NOP
392:   0303  00                  NOP
393:   0304  00                  NOP
394:   0305  00                  NOP
395:   0306  00                  NOP
396:   0307  00                  NOP
397:   0308  00                  NOP
398:   0309  00                  NOP
399:   030A  00                  NOP
400:   030B  00                  NOP
401:   030C  C2FF02              JNZ     ERROR3
402:   030F  7B                  MOV     A,E
403:   0310  C601                ADI     01
404:   0312  5F                  MOV     E,A
405:   0313  C2FF02              JNZ     ERROR3
406:   0316  C3CB02              JMP     ERROR
407:
408:
409:              ;           PRESSURE SUBROUTINE
410:
411:   0319  00      PRESSURE    NOP; INCREMENT OUTPUT
                                      PRESSURE NUMBER
412:   031A  D3E1CDDE03          OUT SHOULDER  !  CALL
                                      DELAY100  !  IN
                                      SHOULDER
413:   0321  C600                ADI     0
414:   0323  FA5702              JM      LOOP10
```

```
415:   0326  D614                SUI     20; THRESHOLD FOR
                                         SHOULDER SENSOR
416:   0328  FA5702              JM      LOOP10   ; JUMP IF
                                                    SENSOR NOT
                                                    PAST
                                                    THRESHOLD
417:   032B  47                  MOV     B,A
418:   032C  D3E2CDDE03          OUT     PRESS  !  CALL DELAY100
                                                !  IN PRESS; INPUT
                                                   SENSOR FOR
                                                   PRESSURE
419:   0333  90                  SUB     B
420:   0334  FA4E03              JM      ROUND10; INCREASE
421:   0337  7A                  MOV     A,D
422:   0338  D601                SUI     1
423:   033A  FA9402              JM      LOOP12
424:   033D  57                  MOV     D,A
425:   033E  C640                ADI     40H
426:   0340  D390                OUT     HAND
427:   0342  D3A0                OUT     THUMB
428:   0344  3E00                MVI     A,0
429:   0346  C601    ROUND20     ADI     1
430:   0348  C24603              JNZ     ROUND20 ; DELAY
431:   034B  C39402              JMP     LOOP12
432:   034E  00      ROUND10     NOP     ; GO ON
433:   034F  7A                  MOV     A,D
434:   0350  C601                ADI     1
435:   0352  FA5702              JM      LOOP10 ; OVERFLOW SO
                                                  GET OUT
436:   0355  57                  MOV     D,A
437:   0356  78                  MOV     A,B
438:   0357  94                  SUB     H  ; CHECK THUMB MAX
439:   0358  F26403              JP      LOOP114
440:   035B  78                  MOV     A,B
441:   035C  C640                ADI     40H
442:   035E  D3A0                OUT     THUMB
443:   0360  3E00                MVI     A,0
444:   0362  D3B0                OUT     EXTENSOR
445:   0364  78      LOOP114     MOV     A,B
446:   0365  95                  SUB     L  ;CHECK HAND MAX
447:   0366  F27203              JP      LOOP123
448:   0369  78                  MOV     A,B
449:   036A  C640                ADI     40H
450:   036C  D390                OUT     HAND
451:   036E  3E00                MVI     A,0
452:   0370  D3B0                OUT     EXTENSOR
453:   0372  3E00    LOOP123     MVI     A,0    ;  DELAY
454:   0374  C601    LOOP124     ADI     1
455:   0376  C27403              JNZ     LOOP124
456:   0379  C39402              JMP     LOOP12
457:
458:
459:
460:
461:           ;                    LENGTH SUBROUTINE
462:
463:
464:   037C  00      LENGTH      NOP     ; INCREMENT OUTPUT BY
                                           LENGTH
```

| | | | | |
|---|---|---|---|---|
| 465: | 037D D3E1CDDE03 | | OUT | SHOULDER  !  CALL DELAY100 IN SHOULDER; INPUT LENGTH OF FINGERS - FLEX NUMBER |
| 466: | 0384 C600 | | ADI | 0 |
| 467: | 0386 FA5702 | | JM | LOOP10 |
| 468: | 0389 D614 | | SUI | 20   ; THRESHOLD FOR LENGTH SENSOR |
| 469: | 038B FA5702 | | JM | LOOP10; JUMP OUT IF SENSOR NOT 0 |
| 470: | 038E 47 | | MOV | B,A |
| 471: | 038F D3E3CDDE03 | | OUT | LEN  !  CALL DELAY100  !  IN LEN  ; OUTPUT LENGTH OF FINGER |
| 472: | 0396 90 | | SUB | B |
| 473: | 0397 FAB103 | | JM | ROUND1  ; INCREASE VOLTS |
| 474: | 039A 7A | | MOV | A,D |
| 475: | 039B D601 | | SUI | 1 |
| 476: | 039D FA9402 | | JM | LOOP12 |
| 477: | 03A0 57 | | MOV | D,A |
| 478: | 03A1 C640 | | ADI | 40H |
| 479: | 03A3 D390 | | OUT | HAND |
| 480: | 03A5 D3A0 | | OUT | THUMB |
| 481: | 03A7 3E00 | | MVI | A,0 |
| 482: | 03A9 C601 | ROUND2 | ADI | 1 |
| 483: | 03AB C2A903 | | JNZ | ROUND2   ;  DELAY |
| 484: | 03AE C39402 | | JMP | LOOP12 |
| 485: | 03B1 00 | ROUND1 | NOP | ; GO ON |
| 486: | 03B2 7A | | MOV | A,D |
| 487: | 03B3 C601 | | ADI | 1 |
| 488: | 03B5 FA5702 | | JM | LOOP10 ; OVERFLOW, SO GET OUT |
| 489: | 03B8 78 | | MOV | A,B |
| 490: | 03B9 94 | | SUB | H  ; CHECK THUMB MAX |
| 491: | 03BA F2C603 | | JP | LOOP214 |
| 492: | 03BD 78 | | MOV | A,B |
| 493: | 03BE C640 | | ADI | 40H |
| 494: | 03C0 D3A0 | | OUT | THUMB |
| 495: | 03C2 3E00 | | MVI | A,0 |
| 496: | 03C4 D3B0 | | OUT | EXTENSOR |
| 497: | 03C6 78 | LOOP214 | MOV | A,B |
| 498: | 03C7 95 | | SUB | L |
| 499: | 03C8 F2D403 | | JP | LOOP223 |
| 500: | 03CB 78 | | MOV | A,B |
| 501: | 03CC C640 | | ADI | 40H |
| 502: | 03CE D390 | | OUT | HAND |
| 503: | 03D0 3E00 | | MVI | A,0 |
| 504: | 03D2 D3B0 | | OUT | EXTENSOR |
| 505: | 03D4 3E00 | LOOP223 | MVI | A,0  ;  DELAY |
| 506: | 03D6 C601 | LOOP224 | ADI | 1 |
| 507: | 03D8 C2D603 | | JNZ | LOOP224 |
| 508: | 03DB C39402 | | JMP | LOOP12 |
| 509: | | | | |
| 510: | | | | |
| 511: | | ;100 MICRO-SECOND DELAY FOR A/D CONVERTER | | |
| 512: | | | | |
| 513: | | DELAY100: | | |
| 514: | 03DE F5 | | PUSH | PSW |

```
515:    03DF    C5                      PUSH    B
516:    03E0    010000                  LXI     B,0
517:                    L100;
518:    03E3    0B                      DCX     B
519:    03E4    78                      MOV     A,B
520:    03E5    B1                      ORA     C
521:    03E6    C2E303                  JNZ     L100
522:    03E9    C1                      POP     B
523:    03EA    F1                      POP     PSW
524:    03EB    C9                      RET
525:
526:
527:    03EC                    END     START;
```

What is claimed is:

1. Apparatus for stimulating controlled contraction of a muscle buried deeply below the skin of a paralyzed person without stimulating contraction of an overlying superficial muscle comprising:

first electrode means comprising at least three electrodes for placement on said skin above said muscles, first stimulation means for applying a pair of alternately pulsed first electrical stimulation signals to said first electrode means at a signal level below that which produces stimulation of said superficial muscle, second electrode means comprising at least three electrodes for placement on said skin alongside said first electrode means, second stimulation means for applying to said second electrode means a pair of alternately pulsed second electrical stimulation signals of like waveform as said first electrical stimulation signals but displaced in phase therefrom by a fixed amount; said second stimulation signals having a signal level below that which produces stimulation of said superficial muscle but above that level which will cooperate with said first electrical stimulation signals to produce controlled contraction of said deeply buried muscle.

2. Apparatus according to claim 1 wherein said second electrical stimulation signals are displaced in phase approximately one millisecond from said first electrical stimulation signals.

3. Apparatus according to claim 1 wherein each of said alternatingly pulsed signals has a frequency of about 60 Hz.

4. Apparatus according to claim 3 wherein said second electrical stimulation signals are displaced in phase approximately one millisecond from said first electrical stimulation signals.

5. Apparatus according to claim 4 wherein said alternatingly pulsed signals comprise pulses having a duration of approximately 300 microseconds.

6. Apparatus for stimulating controlled contraction of a paralyzed muscle comprising:

computing means for generating a digital code representing a desired amplitude of muscle stimulation, a digital to analog converter for converting said digital code to a corresponding analog output, a signal generator responsive to said analog output for generating first, second, third and fourth pulsed stimulation signals having peak amplitudes corresponding to said analog output, said first and second stimulation signals being alternatingly pulsed and said third and fourth stimulation signals having the same waveforms as said first and second stimulation signals respectively but displaced in phase therefrom by a fixed amount, and electrode means for applying said first, second, third and fourth stimulation signals to an area of skin above said muscle.

7. Apparatus according to claim 6 wherein said stimulation signals are each pulsed at a frequency of about 60 Hz.

8. Apparatus according to claim 7 wherein said third and fourth stimulation signals lag said first and second stimulation signals respectively by about one millisecond.

9. Method of stimulating controlled contraction of a deeply buried muscle comprisng the steps of:

positioning first and second sets of electrodes upon an area of skin above said muscle; each of said sets of electrodes comprising two active electrodes and one ground electrode in spaced apart locations along the length of the muscle; corresponding active electrodes of said two sets being spaced side-by-side, applying alternating first and second pulsed stimulation signals to said first set of electrodes at amplitudes which are insufficient for stimulating contraction of superficial muscles overlying said deeply buried muscle, and applying to said second set of electrodes third and fourth stimulation signals which are alternatingly pulsed and delayed in phase a fixed amount with respect to said first and second stimulation signals; said third and fourth stimulation signals having amplitudes which are insufficient for stimulating contraction of said superficial muscles but which cooperate with said first and second pulsed stimulation signals to stimulate controlled contraction of said deeply buried muscle.

10. Method according to claim 9 said third and fourth stimulation signals being delayed with respect to said first and second stimulation signals respectively by a delay which ranges between about 100 microseconds and about 1 millisecond.

11. Method according to claim 10 wherein said delay is about 1 millisecond.

12. Method according to claim 11 wherein each of said stimulation signals is pulsed at a frequency of about 60 Hz.

13. Method according to claim 12 wherein each of said stimulation signals is pulsed by pulses having a duration of about 300 microseconds.

* * * * *